United States Patent [19]

Nixon

[11] 4,193,302
[45] Mar. 18, 1980

[54] METHODS AND APPARATUS FOR EXAMINATION OF SURFACE TEMPERATURE DISTRIBUTION

[75] Inventor: Ralph D. Nixon, Braintree, England

[73] Assignee: English Electric Valve Company Limited, Chelmsford, England

[21] Appl. No.: 941,252

[22] Filed: Sep. 11, 1978

[30] Foreign Application Priority Data

Sep. 15, 1977 [GB] United Kingdom .............. 38452/77

[51] Int. Cl.² .......................... G01D 5/26; G01J 5/26
[52] U.S. Cl. ..................................... 73/351; 73/355 R
[58] Field of Search .............. 73/355 R, 351; 358/113

[56] References Cited

U.S. PATENT DOCUMENTS

| 2,007,118 | 7/1935 | Bosomworth | 73/359 |
| 2,085,508 | 6/1937 | Neubert | 73/355 R |
| 2,366,285 | 1/1945 | Percy et al. | 73/355 R |
| 3,731,536 | 5/1973 | Baumann et al. | 73/351 |
| 3,886,362 | 5/1975 | Miroshnikov | 73/355 R |
| 4,001,497 | 1/1977 | Bosworth | 73/355 R |
| 4,023,201 | 5/1977 | Faulkner | 73/355 R |
| 4,120,200 | 10/1978 | Braun | 73/355 R |

Primary Examiner—Daniel M. Yasich
Attorney, Agent, or Firm—Diller, Ramik & Wight

[57] ABSTRACT

The invention is concerned with monitoring the temperature distribution of a surface which may not be a good emitter of thermal radiation. In the invention a member which is of relatively low thermal conductivity and high thermal emissivity is placed in contact with the surface the temperature distribution of which it is required to monitor so that a thermal image transfers from the latter to the former. A pyroelectric vidicon camera tube then examines the temperature distribution of the member.

7 Claims, 1 Drawing Figure

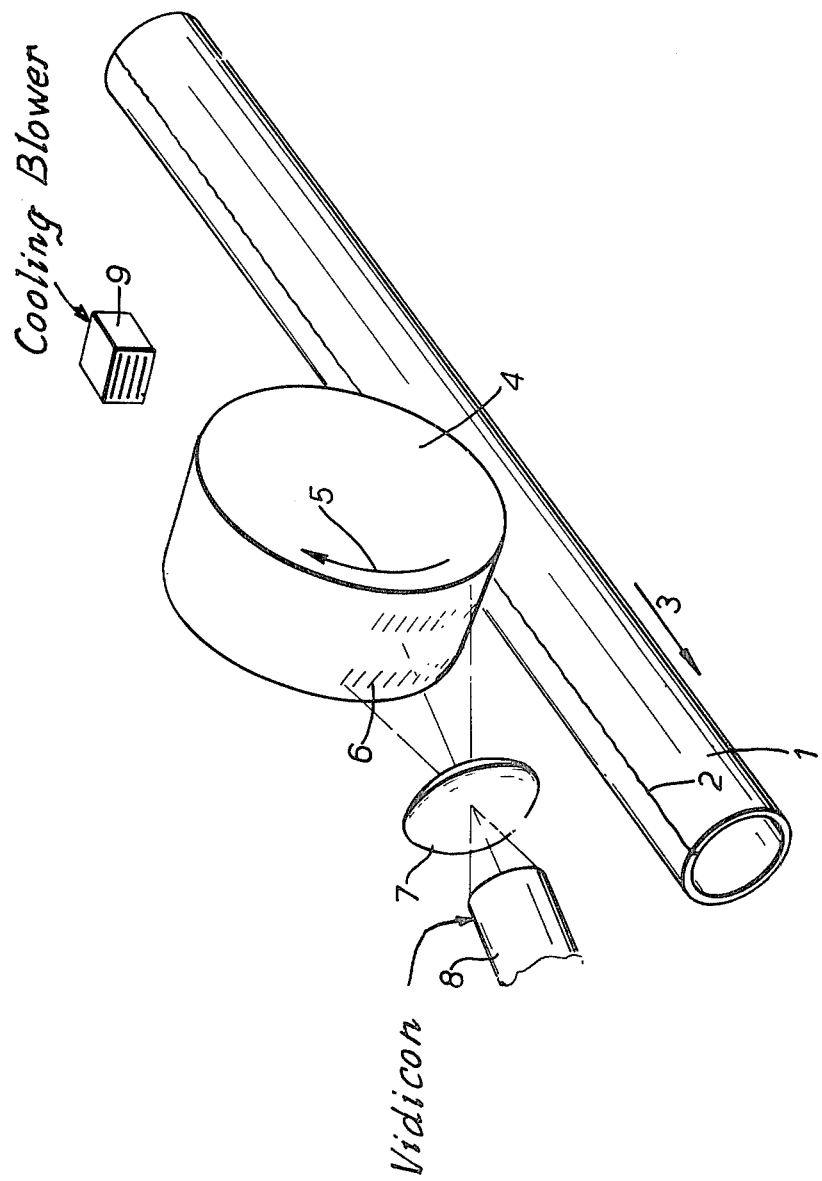

METHODS AND APPARATUS FOR EXAMINATION OF SURFACE TEMPERATURE DISTRIBUTION

This invention relates to methods and apparatus for the examination of surface temperature distribution. It is often required to examine the temperature distribution of a surface using, for example, a thermal radiation sensor such as a pyroelectric vidicon camera. Commonly the temperature distribution as such is not of primary interest, but it is the surface discontinuities which gives rise to variation in the surface temperature which are of primary concern.

A particular example of this is the detection of partial or complete discontinuities in a joining or welding line between two metal surfaces, for example, a welding seam in a tube. Theoretically it is possible to heat the metal on one side of the join and to detect discontinuities in the joint by traversing the seam with a thermal radiation sensor to detect the degree of thermal resistance occasioned by discontinuities in the weld.

However, smooth metal surfaces are, in general, poor emitters of thermal radiation and the smallest temperature differential that can be measured across such surfaces is very much larger, say ten to twenty times larger, than for good emitters. Most bright metal surfaces, for example, have an emission factor $E=0.05$ compared with brick or oxidised steel where $E=0.8$. Thus the effective sensitivity of a thermal radiator sensor viewing a bright metal surface is reduced in a corresponding ratio.

In the case of brass in bright form it is common to find that the emissivity is so low that even very large temperature differences are not detectable.

The present invention seeks to reduce this difficulty.

According to one aspect of this invention a method of monitoring the temperature distribution of a surface of relatively low thermal emissivity comprises the steps of transferring the temperature variation on said surface to a material of relatively low thermal conductivity and relatively high thermal emissivity and examining the surface temperature distribution of said last mentioned material.

According to another aspect of this invention, an arrangement for monitoring the temperature distribution of a body comprises a member of relatively low thermal conductivity and relatively high thermal emissivity, means for causing a surface of said member to contact a surface the temperature distribution of which it is required to monitor so as to effect a transference of a thermal image from the latter to the former and a thermal radiation sensor arranged to examine the temperature distribution of said surface of said member.

Preferably said surface of said member is of black rubber.

Preferably said member is a roller arranged to roll over the surface the temperature distribution of which it is required to monitor and said surface of said member is the rim of the roller.

Preferably said thermal radiation sensor is a pyroelectric vidicon camera tube.

If required a cooling blower may be arranged to assist in the cooling of said surface of said member after the temperature distribution thereof has been examined by said thermal sensor.

The invention is illustrated in and further described with reference to the accompanying drawing which schematically illustrates one arrangement in accordance with the present invention for monitoring the temperature distribution of the surface of a body, in this case a seam welded tube in order to detect properties, such as partial or complete discontinuities in the seam weld.

Referring to the drawing the tube 1, with its welded seam represented at 2, is passed in the direction of arrow 3 beneath a rotatable black rubber roller 4. Roller 4 is rotatable in the direction of the arrow 5, in contact with the welded seam 2.

The interior of the tube 1 is heated by means not shown, so that the temperature distribution over the outer surface of the tube depends upon the degree of thermal resistance occasioned by surface discontinuities in the welded seam 2.

Largely by conduction, a thermal image represented at 6 transfers from the surface of the tube 1 to the rim of the roller 4. This thermal image 6 is focussed by an infra-red lens 7 onto the input of a pyroelectric vidicon camera tube represented at 8 which monitors the thermal distribution of the image on the rim surface of the roller 4.

In order to ensure that the roller surface has attained room temperature once more as it comes into rolling contact with the surface of the tube 1, a cooling blower 9 is arranged to direct a cooling air stream onto the rim surface of the roller 4 after this has been scanned by the pyroelectric vidicon 8.

I claim:

1. An arrangement for monitoring the temperature distribution across the surface of a body, said surface having a relatively low thermal emissivity, said arrangement comprising;
   a transfer member formed of a material of relatively low thermal conductivity and having a contact surface of relatively high thermal emissivity, said transfer member being a roller arranged to roll over said body surface, said contact surface of said roller being the rim (or rolling surface) thereof, said rolling carrying said rolling surface into, and subsequently out of, contact with said body surface, so that said rolling surface is first brought into contact with said body surface thereby effecting a transference of heat in the form of a thermal image from the latter to the former, and is thereafter removed therefrom; and
   a pyroelectric vidicon camera tube arranged to receive and measure thermal radiation emitted by said roller's rolling surface so as to monitor the temperature distribution of said rolling surface, thereby effectively monitoring the temperature distribution across said body surface.

2. An arrangement of evaluating properties of a material forming a body by monitoring the temperature distribution across the surface of the body, said surface having a relatively low thermal emissivity, said arrangement comprising:
   a movable transfer member formed of a material of relatively low thermal conductivity and having a contact surface of relatively high thermal emissivity;
   means for bringing said contact surface of said transfer member into contact with said body surface the temperature distribution of which it is required to monitor, thereby effecting a transference of a thermal image from the latter to the former;
   means for removing said transfer member's contact surface from said body surface; and a thermal radiation sensor arranged to receive and measure thermal radiation emitted by said transfer member's contact surface so as to monitor the temperature distribution of said contact surface, thereby effectively monitoring the temperature distribution across said body surface.

3. An arrangement as claimed in claim 2, wherein said transfer member is formed of black rubber.

4. An arrangement as claimed in claim 2, wherein said transfer member is a roller arranged to roll over said body surface, and said contact surface of said transfer member is the rim (or rolling surface) of said roller, said rolling carrying said rolling surface into, and subsequently out of, contact with said body surface.

5. An arrangement as claimed in claim 2, wherein said thermal radiation sensor is a pyroelectric vidicon camera tube.

6. An arrangement as claimed in claim 2, wherein a cooling blower is arranged to assist in the cooling of said contact surface of said transfer member after the temperature distribution thereof has been monitored by said thermal radiation sensor.

7. A method of evaluating properties of a material forming an article by monitoring the temperature distribution across the surface of the article, said surface having a relatively low thermal emissivity, said method comprising the steps of:

contacting said surface with a movable transfer member formed of a material of relatively low thermal conductivity and having a contact surface of relatively high thermal emissivity;

allowing heat to transfer by conduction from said article to said transfer member, thereby creating on said transfer member's contact surface a thermal image of said article's surface temperature distribution, said thermal image thus giving rise to a corresponding temperature distribution on said contact surface;

removing said transfer member from contact with said article; and measuring the thermal radiation emitted by different areas of said transfer member's contact surface so as to monitor the surface temperature distribution of said contact surface, thereby effectively monitoring the temperature distribution across said article's surface.

* * * * *